US009783325B1

(12) United States Patent
Hierholzer

(10) Patent No.: US 9,783,325 B1
(45) Date of Patent: Oct. 10, 2017

(54) BATH WATER ENHANCING PACKET AND METHOD OF USE

(71) Applicant: Christy Booth Hierholzer, Lighthouse Point, FL (US)

(72) Inventor: Christy Booth Hierholzer, Lighthouse Point, FL (US)

( * ) Notice: Subject to any disclaimer, the term of this patent is extended or adjusted under 35 U.S.C. 154(b) by 412 days.

(21) Appl. No.: 14/599,462

(22) Filed: Jan. 17, 2015

Related U.S. Application Data

(63) Continuation-in-part of application No. 13/205,506, filed on Aug. 8, 2011, now abandoned.
(Continued)

(51) Int. Cl.

| | |
|---|---|
| ***B65B 1/04*** | (2006.01) |
| ***A61K 9/14*** | (2006.01) |
| ***A61K 9/08*** | (2006.01) |
| ***A61K 9/00*** | (2006.01) |
| ***A61K 33/14*** | (2006.01) |
| ***A61K 36/752*** | (2006.01) |
| ***A61K 36/48*** | (2006.01) |
| ***A61K 36/53*** | (2006.01) |
| ***A61K 36/534*** | (2006.01) |
| ***A61K 33/00*** | (2006.01) |
| ***A61K 36/899*** | (2006.01) |

(Continued)

(52) U.S. Cl.
CPC ................ *B65B 1/04* (2013.01); *A61K 9/009* (2013.01); *A61K 9/08* (2013.01); *A61K 33/00* (2013.01); *A61K 33/14* (2013.01); *A61K 36/258* (2013.01); *A61K 36/28* (2013.01); *A61K 36/48* (2013.01); *A61K 36/484* (2013.01); *A61K 36/53* (2013.01); *A61K 36/534* (2013.01); *A61K 36/752* (2013.01); *A61K 36/899* (2013.01); *A61Q 19/10* (2013.01)

(58) Field of Classification Search
CPC ........ A61Q 19/10; A61Q 19/00; A61Q 9/009; A61Q 9/08; A61Q 33/00; A61Q 33/14
USPC .................................. 53/452, 455, 558, 562
See application file for complete search history.

(56) References Cited

U.S. PATENT DOCUMENTS 209,319 A 10/1878 Baronidis
1,465,530 A 8/1923 Smith
(Continued)

FOREIGN PATENT DOCUMENTS

DE 10025677 5/2000

*Primary Examiner* — Christopher Harmon
(74) *Attorney, Agent, or Firm* — Allen D. Hertz, P.A.; Allen D. Hertz

(57) ABSTRACT

A bath water treatment dispensing packet comprising a substance containing body containing a composition of oils, salts, and herbs. The substance containing body comprises two sides of dispensing packet material joined along a peripheral edge forming a containment section therein. The bath water treatment dispensing packet can be provided in a strip having a plurality of containment sections. Each containment section can contain salt or herbs, in an alternating manner. The user would separate the desired quantity of containment sections from the strip and place the separated quantity into the bath water. The salts and/or herbs can be infused with different fragrances of essential oils and colored with natural minerals. The oils are combined with a carrier, such as baking soda, for dry portability until immersed into a fluid. The oils are released into the bath water and float to the surface, providing aromatherapy, as the carrier dissolves.

22 Claims, 12 Drawing Sheets

Related U.S. Application Data

(60) Provisional application No. 61/371,662, filed on Aug. 7, 2010.

(51) Int. Cl.

| | |
|---|---|
| ***A61K 36/28*** | (2006.01) |
| ***A61K 36/484*** | (2006.01) |
| ***A61K 36/258*** | (2006.01) |
| *A61Q 19/10* | (2006.01) |

(56) References Cited

U.S. PATENT DOCUMENTS

| | | | | |
|---|---|---|---|---|
| 2,558,912 | A | 7/1951 | Radelicki | |
| 3,273,704 | A | 9/1966 | Rudiger | |
| 4,659,495 | A | 4/1987 | Figliola | |
| 4,680,916 | A | 7/1987 | Ginn | |
| 4,728,510 | A | 3/1988 | Shibanai et al. | |
| 5,071,704 | A | 12/1991 | Fischel-Ghodsian | |
| 5,403,600 | A | 4/1995 | Reutimann et al. | |
| 5,558,228 | A | 9/1996 | Jackisch et al. | |
| 5,593,635 | A | 1/1997 | Matsumoto et al. | |
| 5,885,701 | A | 3/1999 | Berman et al. | |
| 5,904,028 | A | 5/1999 | Fujiura et al. | |
| 5,916,528 | A | 6/1999 | Matsumoto et al. | |
| 5,958,462 | A | 9/1999 | McLean | |
| 6,090,419 | A | 7/2000 | Popplewell et al. | |
| 6,180,115 | B1 * | 1/2001 | Conrard | A47K 7/03 424/400 |
| 6,289,889 | B1 | 9/2001 | Bell et al. | |
| 6,548,015 | B1 | 4/2003 | Stubbs et al. | |
| 6,800,597 | B2 | 10/2004 | Campagnoli | |
| 6,830,755 | B2 | 12/2004 | Librizzi et al. | |
| 6,906,017 | B1 | 6/2005 | Sonnergren et al. | |
| 7,235,169 | B2 | 6/2007 | Nakamura et al. | |
| 2002/0039868 | A1 | 4/2002 | Shin | |
| 2002/0114850 | A1 | 8/2002 | Camper et al. | |
| 2003/0083211 | A1 | 5/2003 | Ribery et al. | |
| 2003/0114520 | A1 | 6/2003 | Pereira et al. | |
| 2003/0185955 | A1 | 10/2003 | Ghosh et al. | |
| 2003/0228393 | A1 | 12/2003 | Zhao | |
| 2004/0115228 | A1 | 6/2004 | Costa et al. | |
| 2005/0013914 | A1 | 1/2005 | Oku et al. | |
| 2005/0025719 | A1 | 2/2005 | Nussen | |
| 2005/0123651 | A1 | 6/2005 | Hahn et al. | |
| 2006/0128592 | A1 | 6/2006 | Ross et al. | |
| 2006/0172096 | A1 | 8/2006 | Kyle et al. | |
| 2007/0130707 | A1 | 6/2007 | Cohen et al. | |
| 2008/0038375 | A1 | 2/2008 | Park | |
| 2008/0131529 | A1 | 6/2008 | Tao et al. | |
| 2009/0220559 | A1 * | 9/2009 | Feldman | A01N 25/00 424/405 |
| 2011/0250293 | A1 | 10/2011 | Blomberg | |

* cited by examiner

BATH WATER ENHANCING PACKET AND METHOD OF USE

CROSS-REFERENCE TO RELATED APPLICATION

This Non-Provisional Utility Application is a Continuation-In-Part claiming the benefit of U.S. Non-Provisional Utility application Ser. No. 13/205,506 filed on Aug. 8, 2011, which claims the benefit of U.S. Provisional Patent Application Ser. No. 61/371,662, filed on Aug. 7, 2010, which are incorporated herein in their entireties. Aug. 7, 2011 is a Sunday; therefore the applications are co-pending through the next business day (Aug. 8, 2011).

FIELD OF THE INVENTION

The present invention relates to a bath additive packet and method of use, and more particularly, a packet comprising a composition of salts and herbs contained within a porous packet for placement into bath water, whereby the salts and herbs at least partially dissolve into the water.

BACKGROUND OF THE INVENTION

The invention pertains to a bath additive packet and method of use. Baths are one of the most powerful means of affecting the human system in either health or disease. One example is a hot bath with chamomile added for relief of insect bites, aching muscles, and nervousness. A second example is the addition of Eucalyptus to the bath to open the pores while the vapors rising from the steamy bath water help to clear the breathing passages. A third example is the addition of Hyssop, which has a history of use as a cleansing herb and antiseptic. Other examples include the addition of lavender and rosemary, various tonic herbs, soothing herbs, fragrant herbs, and the like. The list is long and the combinations just as numerous.

Salt is a mineral that is composed primarily of sodium chloride. Salts are generally used for flavoring of foods. Salting is additional used for food preservation. Chloride and sodium ions, the two major components of salt, are needed by all known living creatures in small quantities. Salt is involved in regulating the water content (fluid balance) of the body. However, too much salt increases the risk of health problems, including high blood pressure.

Unrefined sea salts are also commonly used as ingredients in bathing additives and cosmetic products. One example is bath salts, which uses sea salt as its main ingredient and combined with other ingredients used for its healing and therapeutic effects. The salts are dispersed directly into the bath water to dissolve.

Plants contain phytochemicals that have effects on the body. There may be some effects when consumed in the small levels that typify culinary "spicing", and some herbs are toxic in larger quantities. Medicinal use of herbs in Western cultures has its roots in the Hippocratic (Greek) elemental healing system, based on a 4-fold elements healing metaphor. Modern pharmaceuticals had their origins in crude herbal medicines, and to this day, many drugs are still extracted as fractionate/isolate compounds from raw herbs and then purified to meet pharmaceutical standards.

Herbs are used as an additive to bath water either directly or via a sachet. Many dried herbs possess a scent and healing properties to maintain and promote physical and psychological well-being.

The manufacturing process for inserting tea leaves or other herbs into a porous bag utilizes sterile equipment, generally fabricated of stainless steel. The material is compatible with tea leaves, herbs, and similar leafy substances. Contrarily, salt and similar sodium based substances corrode the equipment commonly used for the packaging of tea bags and similar packets.

Soylon is a fine mesh made from cornstarch. It was designed for use in fabrication of teabags. It was chosen to replace the materials in teabags, since it can be biodegraded and broken down readily by microorganisms in the soil. It is a safe and non-toxic alternative to the paper bags usually employed.

Accordingly, there remains a need in the art for a device for treating bath water, wherein the device provides a predetermined volume of salts and herbs while retaining the body of the herbs from dispersing within the water.

SUMMARY OF THE INVENTION

The present invention overcomes the deficiencies of the known art and the problems that remain unsolved by providing a method and respective apparatus for enhancing bath water.

In accordance with one embodiment of the present invention, the invention consists of a bath water treatment dispensing packet comprising:

a porous dispensing packet material having a first sheet and a second sheet joined about a peripheral edge forming an interior compartment;

an herb composition deposited within the interior compartment; and a salt composition deposited within the interior compartment.

In a second aspect, the peripheral edge of the bath water treatment dispensing packet is joined by a heat staking process.

Regarding another aspect, the porous dispensing packet material comprises a series of apertures, each aperture having an opening dimension.

In another aspect, one or both of the first and second sheet can be fabricated of a woven material defining a lateral aperture pitch or span and a longitudinal aperture pitch or span.

In yet another aspect, the apertures can be formed in one or both of the first and second sheet.

While in another aspect, the salt composition comprises granular material having a minor dimension that is greater than the opening dimension of each aperture of the porous dispensing packet material, thus maintaining salt composition within the bath water treatment dispensing packet until the packet is placed into bath water.

And in yet another aspect, the herb composition comprises herb flakes having a minor or smallest dimension that is greater than the opening dimension of each aperture of the porous dispensing packet material, thus maintaining the herb composition within the bath water treatment dispensing packet.

Yet another aspect, the peripheral edge of the bath water treatment dispensing packet is joined by a stitching process.

While another aspect, the peripheral edge of the bath water treatment dispensing packet is joined by an ultrasonic welding process.

With yet another aspect, the peripheral edge of the bath water treatment dispensing packet is joined by a folding and sealing process.

Yet another aspect, the peripheral edge of the bath water treatment dispensing packet is joined by a bonding process.

Regarding another aspect, the bath water treatment dispensing packet is segmented into a plurality of composition containment sections by providing a series of section seals.

With yet another aspect, the segments of the bath water treatment dispensing packet are separated by a compartment perforation.

While in another aspect, the bath water treatment dispensing packet is formed comprising an herb compartment containing an herb composition and a salt compartment containing a salt composition.

In yet another aspect, the bath water treatment dispensing packet is folded along a compartment separation provided between the herb compartment and the salt compartment and joined along opposite edges.

With regards to another aspect, the bath water treatment dispensing packet can be deposited into a floating packet dispenser, the floating packet dispenser comprising a porous packet enclosure defining a packet receiving compartment, the porous packet enclosure extending downward from a floatation ring, the porous packet enclosure comprising a float base member disposed proximate a lower edge of the porous packet enclosure.

With yet another aspect, the oil is combined with a carrier, such as baking soda, to store and deliver the oil using a dry medium. The oil may become separated from the carrier upon immersion into the water.

Regarding another aspect, the bath water treatment dispensing packet is formed by folding a base packet material and stitching along each pair of mating edges. The stitching is preferably formed using an overlock stitch. A first overlock stitch is sewn along a first edge, initiating with an entry tail, continuing stitching along the first edge, and finishing with an exit tail. A second overlock stitch is sewn along a second edge, initiating with an entry tail, stitching along the second edge from a folded edge to the first edge, cutting the entry tail of the first overlock stitch, and finishing with an exit tail. A deposit of glue or other sealing material is applied to the intersecting region of the first and second overlock stitches, and the tails cut and removed. The bath water treatment dispensing packet is filled prior to providing a third overlock stitch. The third overlock stitch is sewn along a third and final open edge, initiating with an entry tail, cutting the exit tail of the second overlock stitch, continuing stitching along the third edge, and finishing with an exit tail.

In yet another aspect, a deposit of glue or other sealing material is applied to the intersecting region of the second and third overlock stitches, and the remaining tail cut and removed.

In yet another aspect, a tag is adhesively attached to a distal end of the exit tail of the third overlock stitch.

And with another aspect, a method of use includes the steps of:

obtaining a bath water treatment dispensing packet, the bath water treatment dispensing packet comprising:

- a porous dispensing packet material having a first sheet and a second sheet joined about a peripheral edge forming an interior compartment,
- an herb composition deposited within the interior compartment, and
- a salt composition deposited within the interior compartment;

placing the bath water treatment dispensing packet into a body of bath water;

allowing the herb composition and salt composition to diffuse into the bath water; and placing one's body into the treated bath water.

While another aspect, the bath water treatment dispensing packet further comprises separate compartments for the herb composition and slat composition, whereby the user separates the desired number of herb compartments and salt compartments from the bath water treatment dispensing packet.

And with another aspect, a method further comprises the steps of placing the bath water treatment dispensing packet into a floating packet dispenser and placing the floating packet dispenser into the body of bath water.

In yet another aspect, the method further comprises a step of utilizing the oils to provide aromatherapy.

While in another aspect, the method further comprises a step of allowing the carrier of the oil to dissolve releasing the oils and allowing the oils to float to a surface of the bath water to provide the aromatherapy.

And with another aspect, the method further comprises a step of releasing minerals from the salts into the water.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Detailed embodiments of the present invention are disclosed herein. It will be understood that the disclosed embodiments are merely exemplary of the invention that may be embodied in various and alternative forms. The figures are not necessarily to scale, and some features may be exaggerated or minimized to show details of particular embodiments, features, or elements. Specific structural and functional details, dimensions, or shapes disclosed herein are not limiting but serve as a basis for the claims and for teaching a person of ordinary skill in the art the described and claimed features of embodiments of the present invention. The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims.

Figure 1:
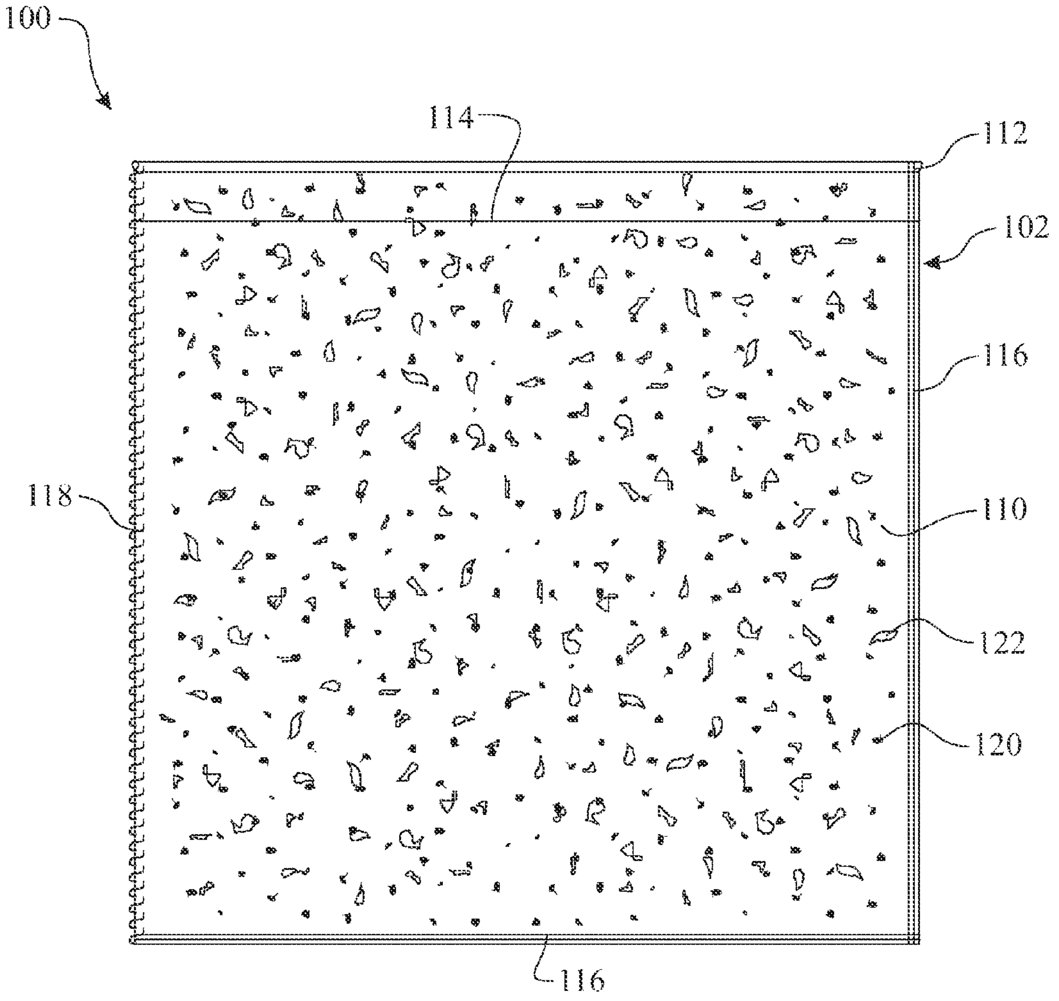
FIG. 1 presents a top plan view of a first exemplary bath water treatment dispensing packet.

For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

A first exemplary bath water treatment dispensing packet is referred to as a bath water treatment dispensing packet 100, as illustrated in FIG. 1. The bath water treatment dispensing packet 100 utilizes a substance containing body 102 for retaining a salt substance 120 and an herb substance 122. The substance containing body 102 is fabricated having two like sized and shaped sections of dispensing packet material 110 bonded together about a perimeter of the sections of the dispensing packet material 110 forming an interior containment area. The dispensing packet material 110 is fabricated of a porous material having pores sized to allow the contents to dissolve into water, while retaining any solid residue. The dispensing packet material 110 can be of any suitable porous material, including a porous paper, soylon, a nylon mesh, a cotton mesh, a silk mesh, and the like. It is preferred that the dispensing packet material 110 is of a biodegradable material. The edges are sealed by any known means respective to the selected material. The exemplary edge sealing means include folding an edge as illustrated along a top edge having a material fold section 112 which is adhered to one of the sections of the dispensing packet material 110 by a fold seal 114; a ultrasonic seal 116 as illustrated along the right edge and lower edge; and a stitched seal 118 as illustrated along a left edge. The stitched seal 118 can be provided using a standard sewing machine; an overlock sewing machine (commonly referred to as a serger), which additionally trims any excess material; and the like. Other sealing means, such as heat sealing, utilization of a bonding substance, and the like, can be used for joining any of the edges of the bath water treatment dispensing packet 100.

The material would pass under a dispensing apparatus that dispenses a salt substance 120 and an herb substance 122 onto the material. A second layer of material is placed over the composition of salt 120 and herbs 122. The herbs 122 can include: rose, lavender, chamomile, jasmine, rosemary, ginger, eucalyptus, peppermint, spearmint, sage, lemongrass, thyme, comfrey, violets, and the like. The salt substance 120 is preferably any or a combination of Epsom salt; sea salt, dead sea salt, Himalayan salt, Pacific salt, Brittany or any other form of unrefined salts; earth salt; roasted salt; iodized salt; and the like. The salt can be provided in any grain size, including fine, medium, and coarse, or any combination thereof. The salt 120 can be infused with different fragrances of essential oils and colored with natural minerals.

It is preferred to dispense the salt substance 120 and herb substance 122 separately to utilize equipment compatible with each of the substances. The edges of the layers are joined by any reasonable joining means such as those described above. Alternately, the two layers of material 110 can have three sides joined. The packet would have the interior compartment portion opened along the un-joined edge, the composition of salt 120 and herbs 122 would be dispensed therein, and the un-joined edge sealed by any reasonable joining means such as those described above. Once the entire periphery of the dispensing packet material 110 is sealed, the composition of salt 120 and herbs 122 is encased therein.

Figure 2:
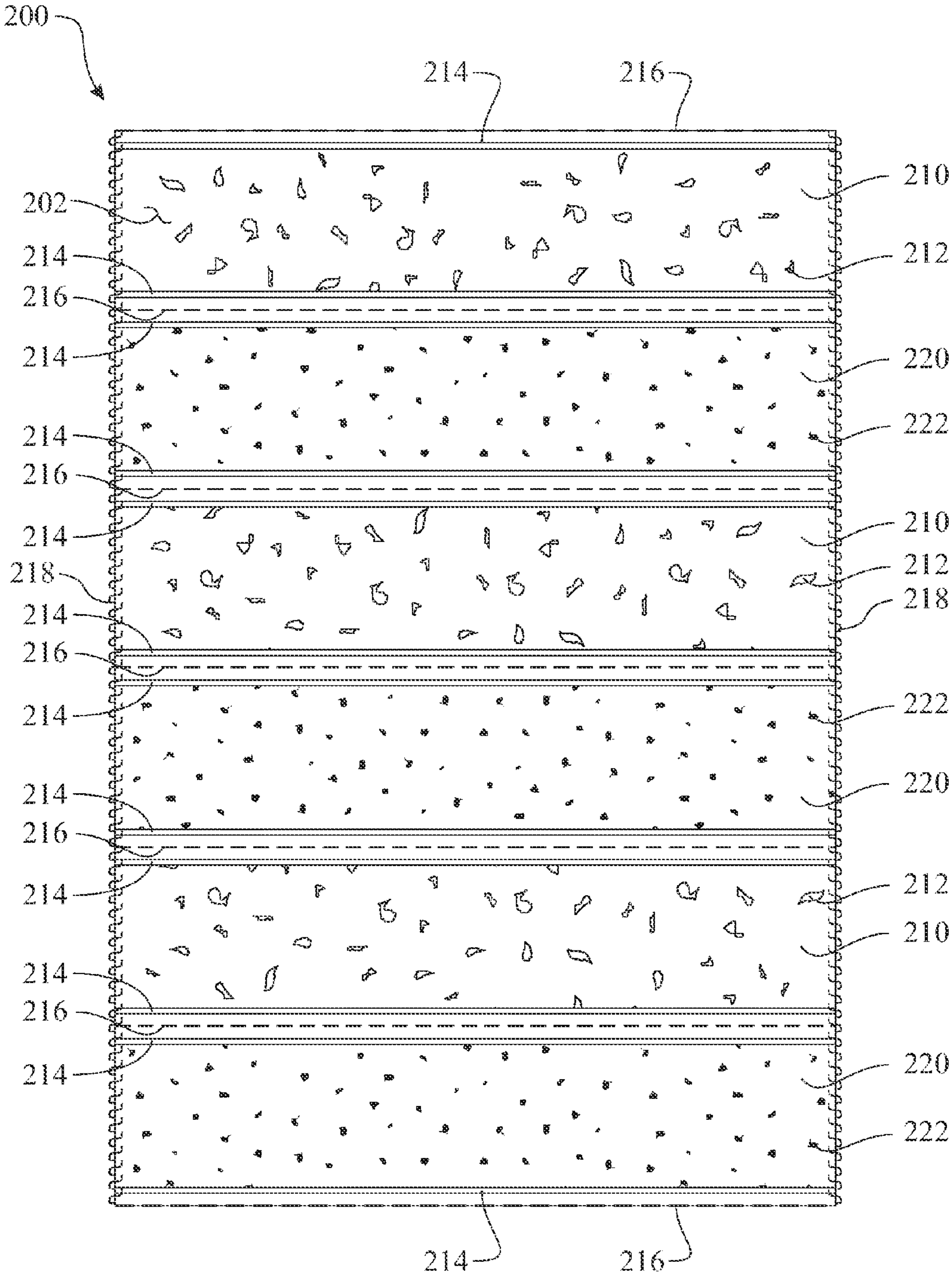
FIG. 2 presents a top plan view of a second exemplary bath water treatment dispensing packet comprising a plurality of composition compartments.

A second exemplary bath water treatment dispensing packet is referred to as a bath water treatment dispensing packet strip 200, as illustrated in FIG. 2. The bath water treatment dispensing packet strip 200 is fabricated having two like sized and shaped sections or continuous rolls of dispensing packet material 202 bonded together along each of the two parallel longitudinal edges, such as by the stitched seal 218. It is understood that any joining means can be utilized to join each of the mating longitudinal edges of the bath water treatment dispensing packet strip 200. A plurality of section seals 214 is created laterally, spanning between each of the two parallel longitudinal edges, creating a plurality of containment areas. In the exemplary embodiment illustrated in FIG. 2, the bath water treatment dispensing packet strip 200 is fabricated comprising a series of alternating herb compartments 210 and salt compartments 220. An herb substance 212 is deposited within each herb compartment 210. A salt substance 222 is deposited within each salt compartment 220. A compartment perforation 216 is cut between each pair of adjacent containment areas providing an aid for separating the desired number of containment areas from the bath water treatment dispensing packet strip 200. In an alternate embodiment, the containment areas can be provided to hold a composition comprising both salt substance 120 and herb substance 122.

Figure 3:
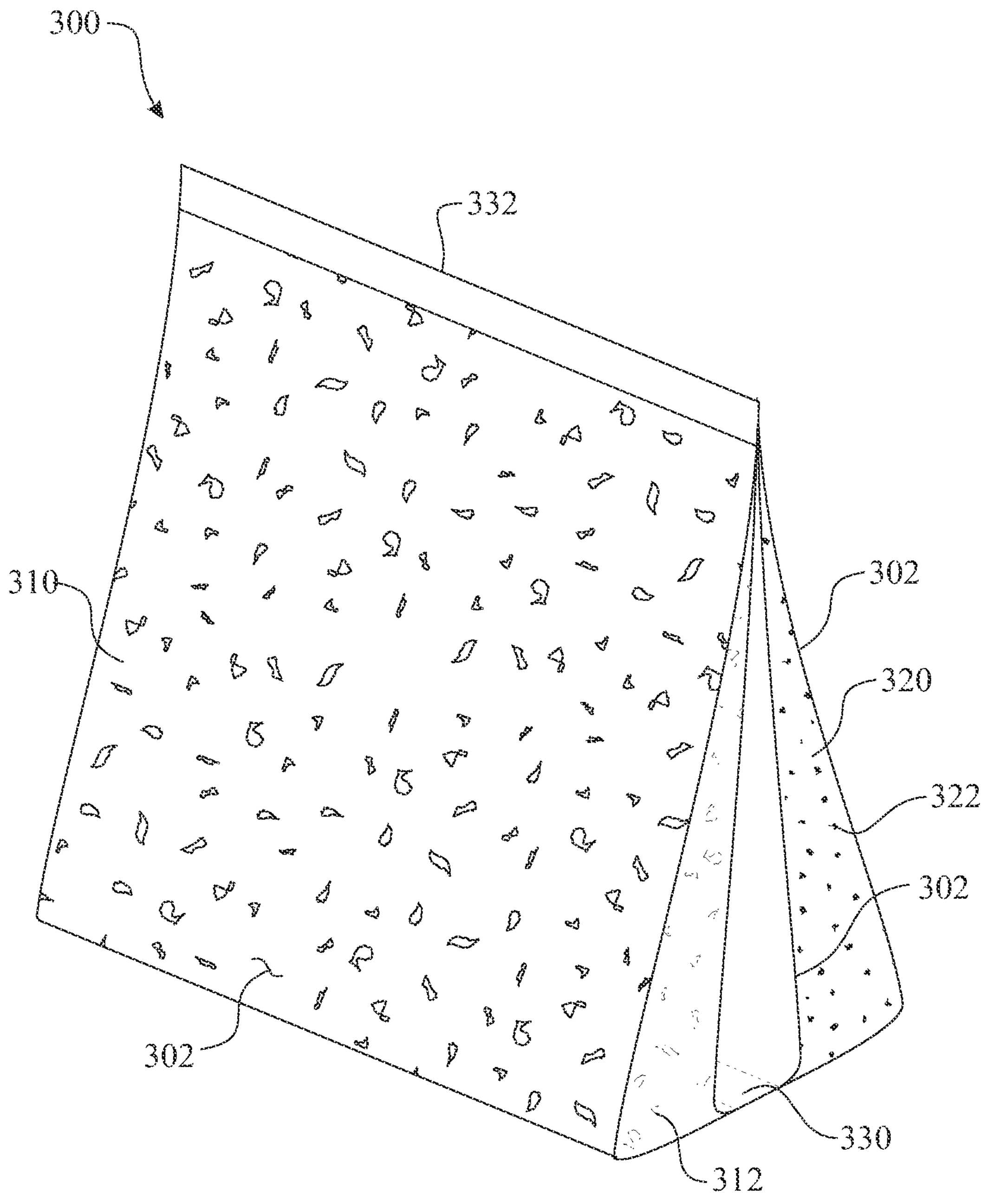
FIG. 3 presents an isometric view of a third exemplary bath water treatment dispensing packet.

A third exemplary bath water treatment dispensing packet is referred to as a bath water treatment dispensing packet 300, as illustrated in FIG. 3. The bath water treatment dispensing packet 300 is fabricated having two like sized and shaped containment sections referred to as an herb compartment 310 and a salt compartment 320. The herb compartment 310 and salt compartment 320 are formed using a pair of continuous rolls of dispensing packet material 302 bonded together along each of the two parallel longitudinal edges. A compartment separation 330 is created between the herb compartment 310 and the salt compartment 320 by any reasonable joining method provided between the two layers of the material. The herb compartment 310 and salt compartment 320 can be formed having a three-dimensional shape incorporating additional surfaces of the dispensing packet material 302, such as end sheets. The bath water treatment dispensing packet 300 can be folded about the compartment separation 330 and joined along two distal edges folded against one-another and joined by any reasonable method. The joining can be provided by any reasonable joining means, including stitching, a packet shaping adhesion 332 (as shown), a staple, and the like. It is understood the herb substance 312 and the salt substance 322 can be combined as a single composition and deposited into each of the two compartments. The compartment separation 330 may be optional for an embodiment where the substances are combined into a single composition.

Figure 4:
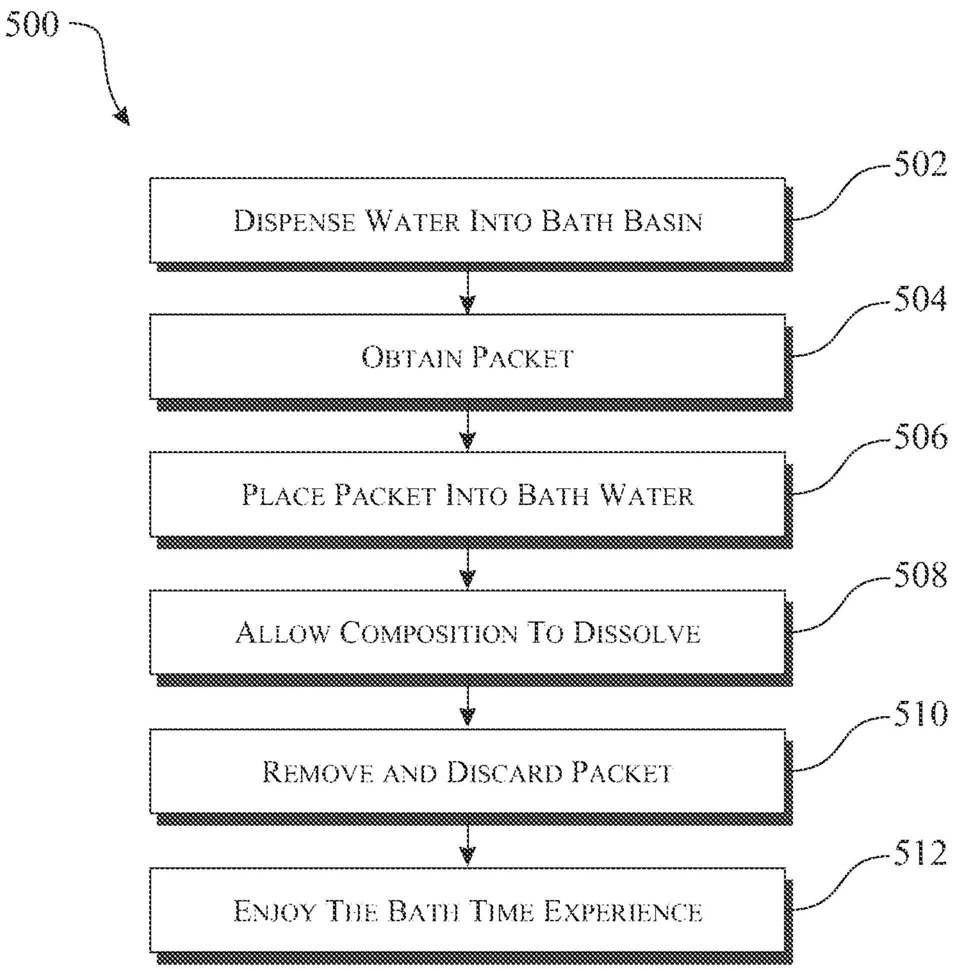
FIG. 4 presents an exemplary flow diagram of a first method of use of the bath water treatment dispensing packet.
Figure 5:
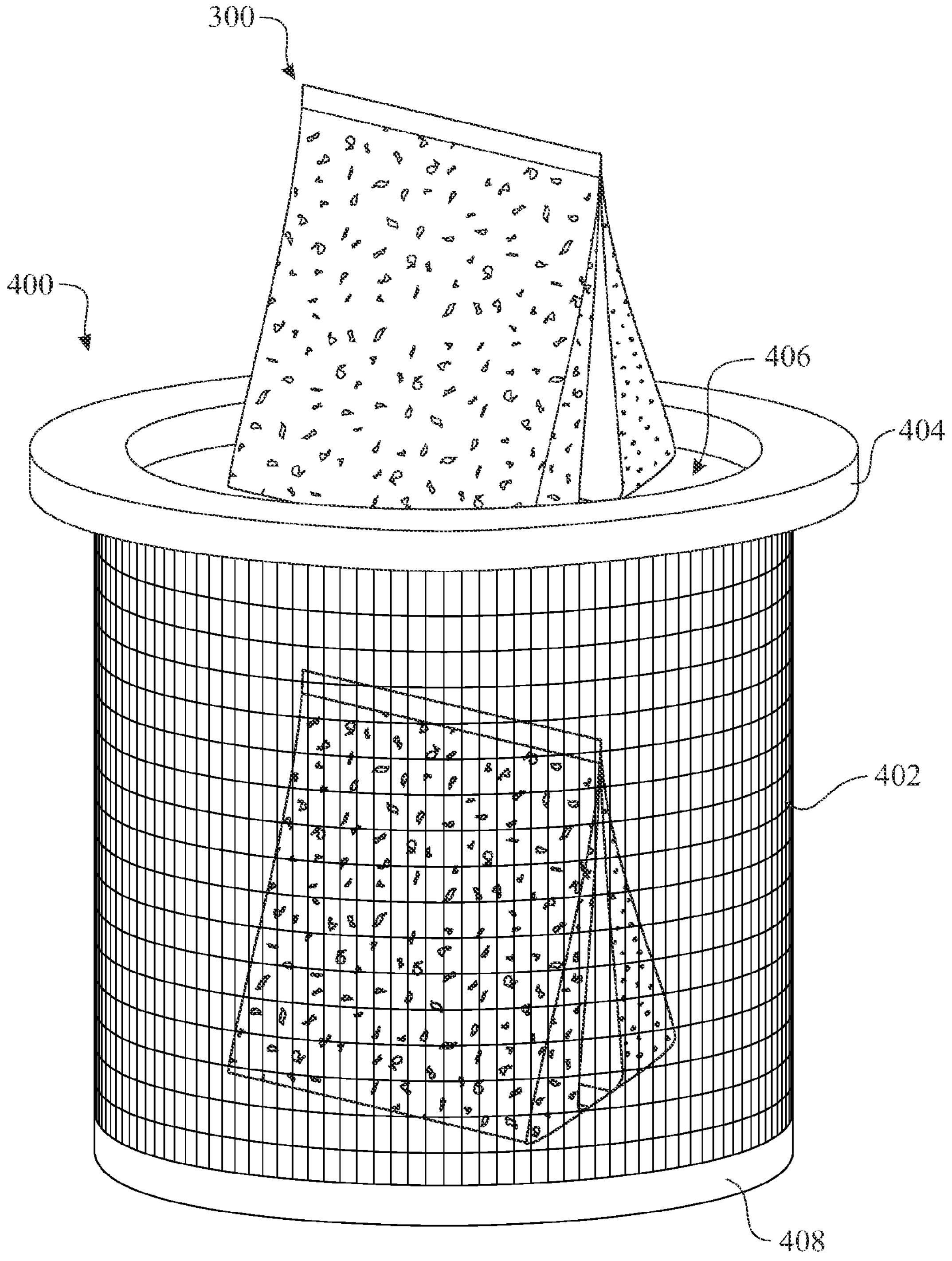
FIG. 5 presents an optional floating packet dispenser for use in conjunction with the bath water treatment dispensing packet.

The bath water treatment dispensing packet is used in accordance with a bath additive method of use flow diagram 500 illustrated in FIG. 4. The bath additive method of use flow diagram 500 initiates with a dispensing water into a bath basin step 502. The bather would determine the desired bath temperature and set valves providing the source water accordingly. The bather would continue with a step of obtaining a bath water treatment dispensing packet 504. The bather then places the bath water treatment dispensing packet into the body of bath water 506. The bather leaves the bath water treatment dispensing packet 100 within the body of bath water, allowing the salt substance 120 and herb substance 122 to dissolve 508 within the bath water. The bather can optionally remove and discard the packet 510 if desired. Alternately, the bather can leave the packet within the bath water. The bather then places themselves into the body of bath water and enjoys the experience 512.

An optional floating packet dispenser 400 can be utilized to contain one or more bath water treatment dispensing packets 100, a series of containment compartments 210, 220, or one or more bath water treatment dispensing packets 300. The floating packet dispenser 400 includes a floatation ring 404 having an opening providing access to a packet receiving compartment 406. The packet receiving compartment 406 is formed by a porous packet enclosure 402, which extends downward from the floatation ring 404 from a first end of the porous packet enclosure 402. The porous packet enclosure 402 is preferably a tubular shaped, porous material having a bottom. A float base member 408 attached thereto at an opposite end of the porous packet enclosure 402 may form the bottom. The exemplary porous packet enclosure 402 is fabricated of a screening material, such as a polyester mesh. It is preferred that the components of the floating packet dispenser 400 be fabricated of anti-corrosive materials to ensure longevity of the floating packet dispenser 400. The selection of materials is critical, as the floating packet dispenser 400 is exposed to water, air, salts, and herbs; a combination that is conducive to corrosion.

Figure 6:
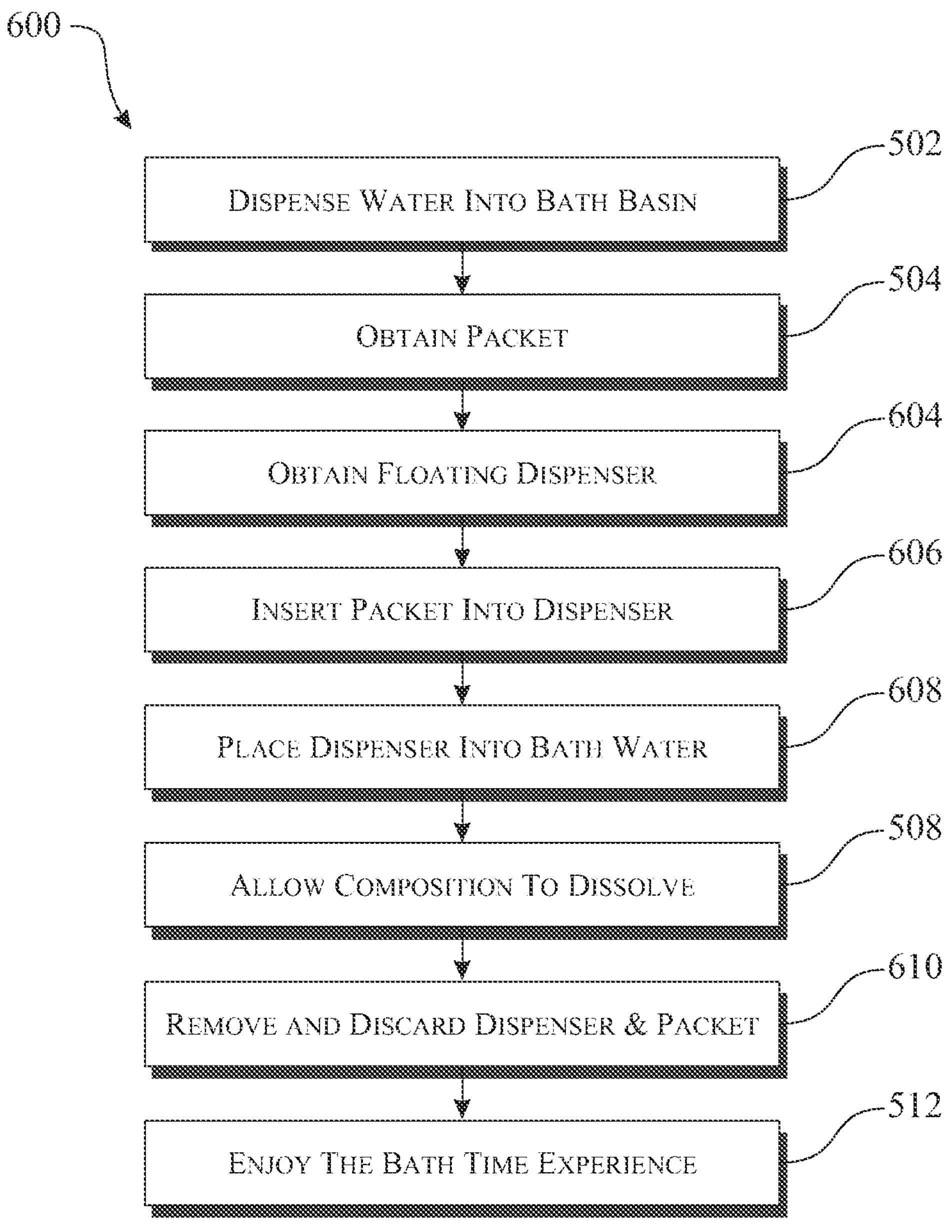
FIG. 6 presents an exemplary flow diagram of a second method of use of the bath water treatment dispensing packet utilizing the floating packet dispenser.
Figure 7:
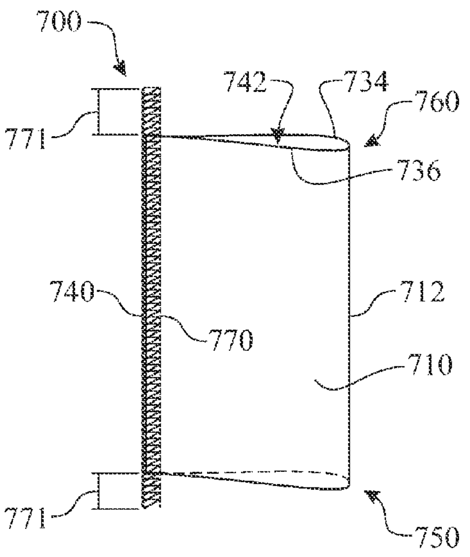
FIG. 7 presents a side elevation view of a first step of an exemplary packet fabrication.
Figure 8:
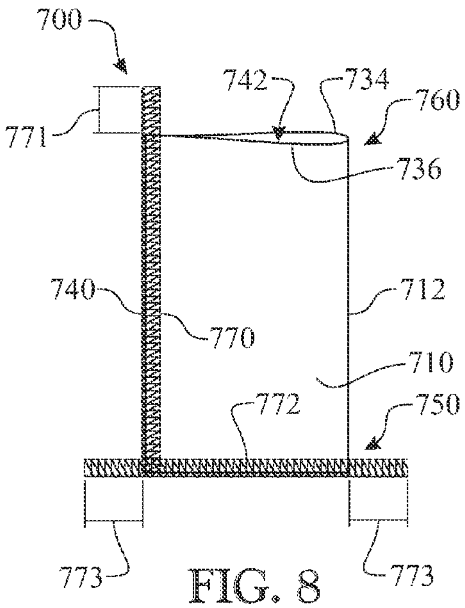
FIG. 8 presents a side elevation view of a second step of an exemplary packet fabrication.
Figure 9:
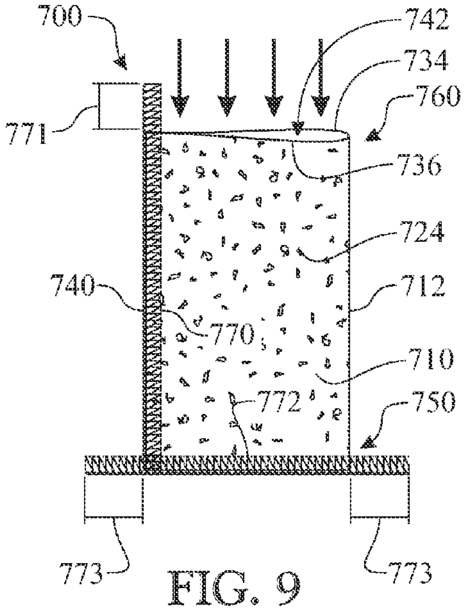
FIG. 9 presents a side elevation view of a third step of an exemplary packet fabrication.
Figure 10:
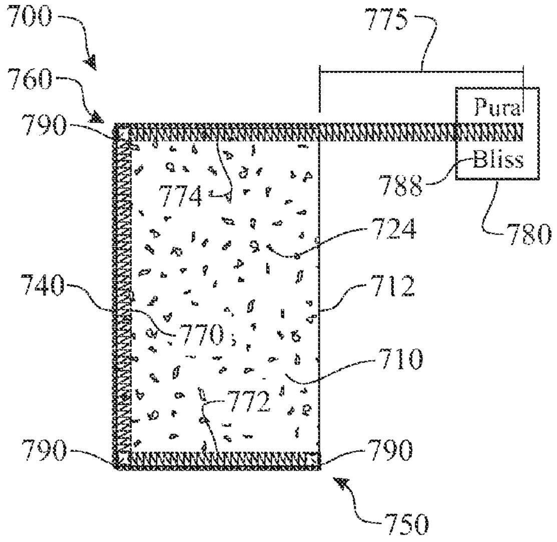
FIG. 10 presents a side elevation view of a fourth step of an exemplary packet fabrication.

The bath water treatment dispensing packet can optionally be used in accordance with a bath additive method of use flow diagram 600 illustrated in FIG. 6. The bath additive method of use flow diagram 600 is similar to the bath additive method of use flow diagram 500 initiating with the dispensing water into a bath basin step 502. The bather would determine the desired bath temperature and set valves providing the source water accordingly. The bather would continue with the step of obtaining a bath water treatment dispensing packet 504. The bath additive method 600 diverts from the bath additive method 500 whereby the bather inserts the packet 100 into the dispenser 400 in accordance with an insert packet into the dispenser step 606. The bather then places the dispenser 400 into the body of bath water 608. The bather leaves the bath water treatment dispensing packet 100 within the body of bath water, allowing the salt substance 120 and herb substance 122 to dissolve 508 within the bath water. The bather can optionally remove the dispenser and discard the packet 610 if desired. Alternately, the bather can leave the packet within the bath water. The bather then places themselves into the body of bath water and enjoys the experience 512.

In addition to the considerations of the substances, the temperature of the bath water plays an important role in the effectiveness of the bath. A cold bath stimulates the system, and should be brief. A warm to hot bath provides better relief for aching muscles and joints, as well as producing perspiration, which opens the bather's pores, allowing better absorption of the salt substance 120 and the herb substance 122. A hot bath should be followed by a cool shower or spray to close the bather's pores. Recommended temperatures are 96 to 98 degrees F. for hot baths; 92 degrees F. for a refreshing bath; and 70 to 85 degrees F. for a peppy bath.

An exemplary fabrication process of a bath water treatment dispensing packet 700 is presented in a series of fabrication steps illustrated in FIGS. 7 through 10. In a first step, a sheet of dispensing packet material 710 is cut into the desired shape. The dispensing packet material 710 is preferably an organic material having a porosity allowing a carrier (such as baking soda), and salts to dissolve and pass therethrough when immersed in a liquid. The dispensing packet material 710 is folded along a packet material fold 712, aligning each of the exposed edges 740, 750, 760. The folding process defines a first packet side 734 and a second packet side 736 from the dispensing packet material 710. In the exemplary embodiment, the dispensing packet material 710 is cut into a square or rectangular shape and folded along the packet material fold 712 forming a smaller square or rectangular shape having three unsecured edges 740, 750, 760 and a packet material fold 712. A first packet stitch 770 is formed along a first packet seam edge 740, preferably using an overlock machine. The overlock stitch machine forms a weave between a plurality of threads. The weave or stitch initiates prior to contact with the material forming a first stitch tail 771. The tailor or seamstress continues running the machine along the entire first packet seam edge 740, continuing past the distal end, forming a second first stitch tail 771. The tailor or seamstress continues, rotating the bath water treatment dispensing packet 700 and creates a second packet stitch 772 along a second packet seam edge 750, between the packet material fold 712 and the first packet seam edge 740, passing over the first packet stitch 770. As the second packet stitch 772 passes across the first packet stitch 770, the overlock machine shears the respective first stitch tail 771 from the first packet stitch 770. The overlap between the second packet stitch 772 and the first packet stitch 770 increases reliability of the seam by ensuring against unraveling of the stitching. An oil-salt-herb composition 724 is separately mixed, then a predetermined volume is dispensed into an interior of the bath water treatment dispensing packet 700 through a packet fill opening 742. The tailor or seamstress continues, rotating the bath water treatment dispensing packet 700 and creates a third packet stitch 774 along a third packet seam edge 760, between the packet material fold 712 and the first packet seam edge 740, passing over an opposite end of the first packet stitch 770. As the third packet stitch 774 passes across the first packet stitch 770, the overlock machine shears the respective first stitch tail 771 from the first packet stitch 770. The overlap between the third packet stitch 774 and the first packet stitch 770 increases reliability of the seam by ensuring against unraveling of the stitching.

Figure 11:
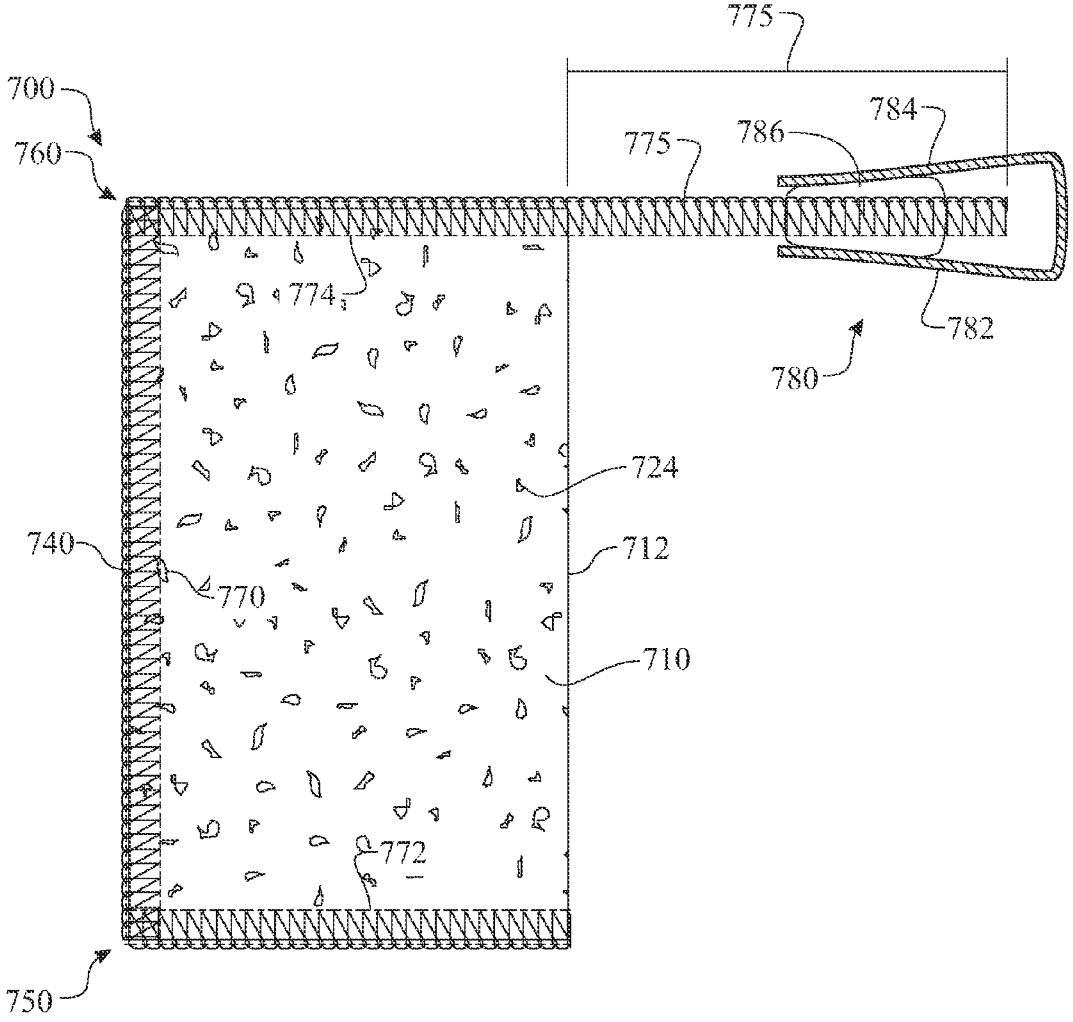
FIG. 11 presents a side elevation view including a sectioned side view detailing an assembly of a tag.

Adhesive or other sealant 790 is applied to each end of the second packet stitch 772 to help ensure against unraveling of the stitching. Each tail second stitch tail 773 is manually cut from the second packet stitch 772 at each end of the second packet seam edge 750. Adhesive or other sealant 790 may be applied to one or both ends of the third packet stitch 774 to help ensure against unraveling of the stitching. One or both tails 775 are manually cut from the third packet stitch 774 at each end of the third packet seam edge 760. Where adhesive or other sealant 790 is applied to one end of the third packet stitch 774, a tag 780 would be adhesively attached to a distal end of the third stitch tail 775. The tag 780 is folded in half (defining a first tag side 782 and a second tag side 784) and adhesively secured to the distal end of the third stitch tail 775 as illustrated in FIG. 11. A volume of adhesive 786 is dispensed between mating interior surface of the first tag side 782 and second tag side 784. The first tag side 782 and second tag side 784 are brought together, compressing the respective portion of the third stitch tail 775. The tag 780 can include indicia 788. The indicia 788 can include branding information, marketing information, composition information, manufacturing information, and the like.

Figure 12:
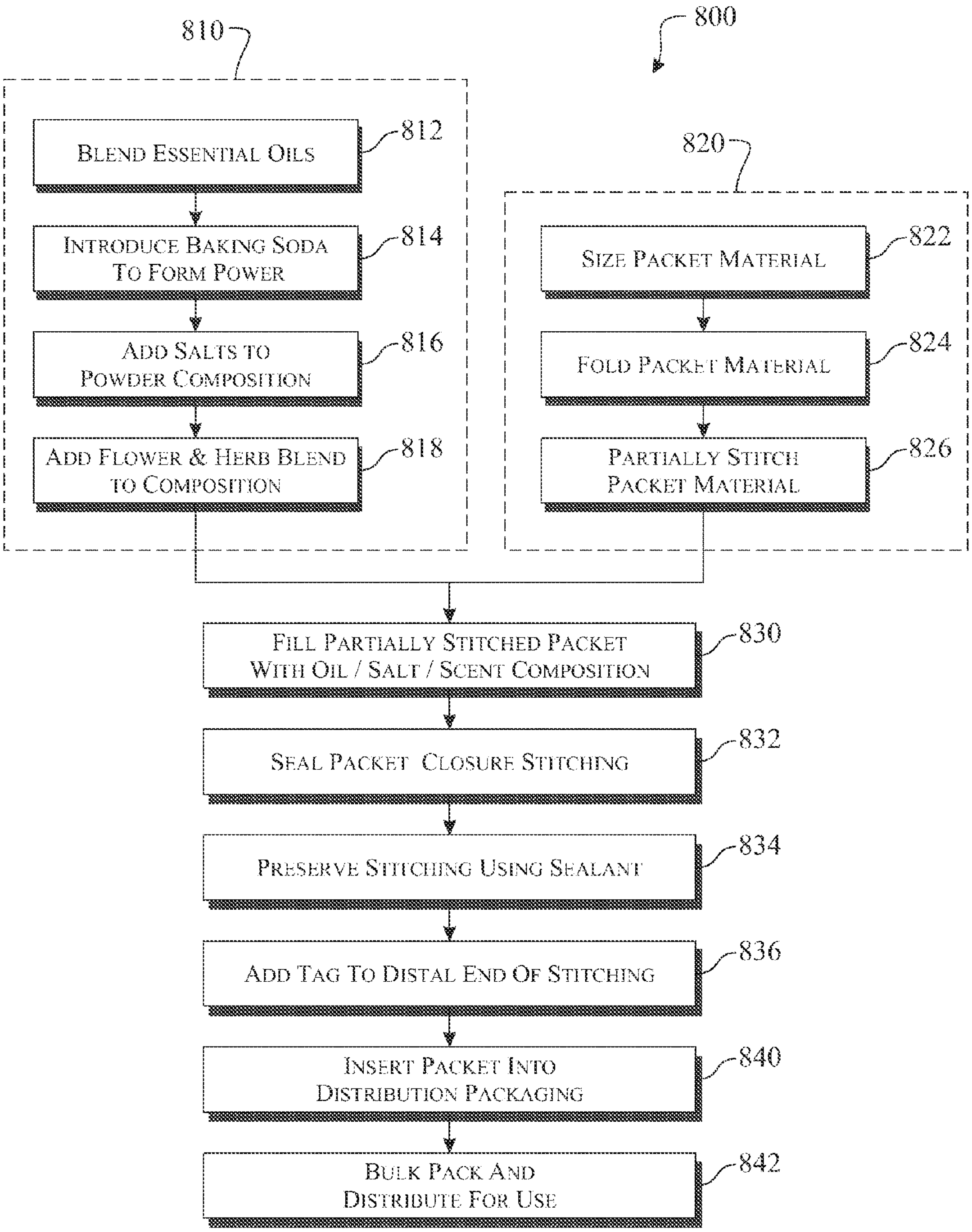
FIG. 12 presents an exemplary packet fabrication flow diagram.

One exemplary embodiment for fabricating the bath water treatment dispensing packet 700 is presented in a packet fabrication flow diagram 800 illustrated in FIG. 12. A first branch of the packet fabrication flow diagram 800 includes a composition blending process 810 that details exemplary steps for creating the oil-salt-herb composition 724. The composition blending process 810 initiates with a step of blending a quantity of essential oils 812 to create an oil mixture. The oil mixture may comprise at least one selected oil. A quantity of an oil carrier, such as baking soda, is introduced into the oil mixture to absorb the oil mixture as presented in block 814, wherein the oil carrier is utilized for conveying the oil mixture in a dry configuration. The oil carrier subsequently dissolves when immersed within a liquid, thus releasing the oils into the liquid. It is recognized that any oil carrier capable of meeting the subject requirements may be used to absorb the oil. Once the oil is absorbed into the oil carrier, a quantity of at least one salt composition is introduced into the oil and salt blended composition, as indicated in block 816. It is preferred that a blend of salt compositions are combined and introduced into the oil and salt blended composition. The oils may include scents to enhance the overall bathing experience. Finally, a flower and herb blend is created and introduced into the oil and salt blended composition. The flower and herb blend may be crushed into a particle size allowing the flower and herb blend to pass through the pores of the dispensing packet material 710 or they may be sized to be retained within the interior compartment of the porous bath water treatment dispensing packet.

A second branch of the packet fabrication flow diagram 800 includes a packet preparation process 820 that details exemplary initial steps for creating the packet. The packet preparation process 820 initiates with a step of cutting a sheet of raw dispensing packet material 710 into a desired size in accordance with block 822. The dispensing packet material 710 is preferably of a porous organic material. The sized dispensing packet material 710 is then folded in half along a packet material fold 712 as described in block 824. A portion of the mating edges is joined using an overlock stitch to form a containment packet having an opening; the step being summarized in block 826. At this point in the process, the dispensing packet material 710 is folded into two sizes with a portion of the edges joined to form a container comprising an opening along one edge. The ends of each stitch may be preserved by applying a sealant 790 at each end thereof.

The blended composition is dispensed into the container through the open edge, as described in block 830. Once the desired volume of the blended composition is dispensed into the packet, the open seam is joined with a closure stitch as directed by block 832. The closure stitch is preserved by applying a sealant 790 at one or both ends of the stitch in accordance with block 834. In the embodiment where the sealant 790 is applied at one end of the stitch, a tag would be adhered to the remaining tail of the stitch in accordance with block 836. The bath water treatment dispensing packet 700 is inspected either randomly or individually, then the bath water treatment dispensing packet 700 is placed into a distribution packaging as directed within block 840. The distribution packaging is preferably a plastic bag, which confines the various ingredients and odors of the blended composition when sealed. The bath water treatment dispensing packet 700 may be placed individually or in multiples into each distribution package. Multiple bulk packages are placed into a bulk pack for distribution to retailers as referenced in block 842. The bulk pack may be plastic containers, boxes, crates, and the like.

The ingredients for the oil-salt-herb composition 724 can be provided in a variety of mixes. The exemplary mixes could be applicable for any of the embodiments disclosed herein. The following are three exemplary ingredient lists for three distinct variations of the oil-salt-herb composition 724.

A basic or generic exemplary composition of the oil-salt-herb composition 724 preferably includes:

TABLE 1

Organic Bath Bags Ingredients - Generic Composition
Organic Bath Bags Ingredients - Generic Composition

| Ingredient | Variance | General Variance | Desired Variance |
|---|---|---|---|
| General Natural Salts | 50-96% | 70-85% | 74-83% |
| Epsom Salt | 1.0-30% | 8.0-19% | 11-16% |
| Oil Carrier/Baking Soda | 2.0-8.0% | 3.0-5.0% | 3.3-4.5% |
| Oil/Oil Blend | 0.5-10.0% | 0.5-6.0% | 0.5-3.0% |
| Herbs & Flowers | 0.0-50% | 2.0-25% | 3.0-15% |

A first exemplary oil-salt-herb composition 724 is referred to as a mint based composition and is presented below in Table 2.

TABLE 2

Organic Bath Bags Ingredients - Mint Based Composition
Organic Bath Bags Ingredients - Mint Based Composition

| Ingredient | Variance | General Variance | Desired Variance |
|---|---|---|---|
| Dead Sea Salt | 50-96% | 70-85% | 74-83% |
| Epsom Salt | 1.0-30% | 8.0-19% | 11-16% |
| Baking Soda | 2.0-8.0% | 3.0-5.0% | 3.3-4.5% |
| Milk Thistle | 0.0-4.0% | 0.0-3.0% | 0.5-2.5% |
| Peppermint Leaf | 0.0-4.0% | 0.0-3.0% | 0.5-2.5% |
| Peppermint Oil | 0.0-1.3% | 0.0-0.6% | 0.05-0.4% |

TABLE 2-continued

Organic Bath Bags Ingredients - Mint Based Composition
Organic Bath Bags Ingredients - Mint Based Composition

| Ingredient | Variance | General Variance | Desired Variance |
|---|---|---|---|
| Lavendin Oil | 0.0-1.3% | 0.0-0.6% | 0.05-0.4% |
| Eucalyptus Oil | 0.0-1.3% | 0.0-0.6% | 0.05-0.4% |
| Geranium Oil | 0.0-1.3% | 0.0-0.6% | 0.05-0.4% |
| Cedarwood Oil | 0.0-1.0% | 0.0-0.3% | 0.05-0.15% |
| Eleuthero Root Ginseng | 0.0-8.5% | 0.0-4.5% | 0.0-4.0% |
| Licorice | 0.0-8.5% | 0.0-4.5% | 0.0-4.0% |
| Burdork Root | 0.0-8.5% | 0.0-4.5% | 0.0-4.0% |
| Rooibos | 0.0-8.5% | 0.0-4.5% | 0.0-4.0% |

A second exemplary oil-salt-herb composition 724 is referred to as a lavender based composition and is presented below in Table 3.

TABLE 3

Organic Bath Bags Ingredients - Lavender Based Composition
Organic Bath Bags Ingredients - Lavender Based Composition

| Ingredient | Variance | General Variance | Desired Variance |
|---|---|---|---|
| Andes Rose Salt | 50-96% | 70-85% | 74-83% |
| Epsom Salt | 1.0-30% | 8.0-19% | 11-16% |
| Baking Soda | 2.0-8.0% | 3.0-5.0% | 3.3-4.5% |
| Lavender Flowers | 1.0-7.0% | 1.0-5.0% | 2.0-4.0% |
| Lavender Oil | 0.0-1.8% | 0.0-1.0% | 0.15-0.8% |
| Chamomile Oil | 0.0-1.3% | 0.0-0.6% | 0.05-0.4% |
| Rosewood Oil | 0.0-1.0% | 0.0-0.3% | 0.05-0.15% |
| Sweet Orange Oil | 0.0-1.0% | 0.0-0.3% | 0.05-0.15% |
| Petitgrain Oil | 0.0-1.0% | 0.0-0.3% | 0.05-0.15% |
| Bergamot Oil | 0.0-1.5% | 0.0-0.3% | 0.00-0.15% |
| Palmarosa Oil | 0.0-1.5% | 0.0-0.3% | 0.00-0.15% |
| Chamomile Flowers | 0.0-8.5% | 0.0-4.5% | 0.0-4.0% |
| Lemongrass | 0.0-8.5% | 0.0-4.5% | 0.0-4.0% |
| Bergamot | 0.0-8.5% | 0.0-4.5% | 0.0-4.0% |

A third exemplary oil-salt-herb composition 724 is referred to as a citrus based composition and is presented below in Table 4.

TABLE 4

Organic Bath Bags Ingredients - Citrus Based Composition
Organic Bath Bags Ingredients - Citrus Based Composition

| Ingredient | Variance | General Variance | Desired Variance |
|---|---|---|---|
| Himalayan Salt | 50-96% | 70-85% | 74-83% |
| Epsom Salt | 1.0-30% | 8.0-19% | 11-16% |
| Baking Soda | 2.0-8.0% | 3.0-5.0% | 3.3-4.5% |
| Green Rooibos | 0.0-4.0% | 0.0-3.0% | 0.5-2.5% |
| Orange Peel | 0.0-4.0% | 0.0-3.0% | 0.5-2.5% |
| Sweet Orange Oil | 0.0-1.8% | 0.0-1.0% | 0.15-0.8% |
| Lavender Oil | 0.0-1.8% | 0.0-0.9% | 0.15-0.7% |
| Citrus Petitgrain Oil | 0.0-1.3% | 0.0-0.6% | 0.05-0.4% |
| Blood Orange Oil | 0.0-1.0% | 0.0-0.3% | 0.05-0.15% |

Figure 13:
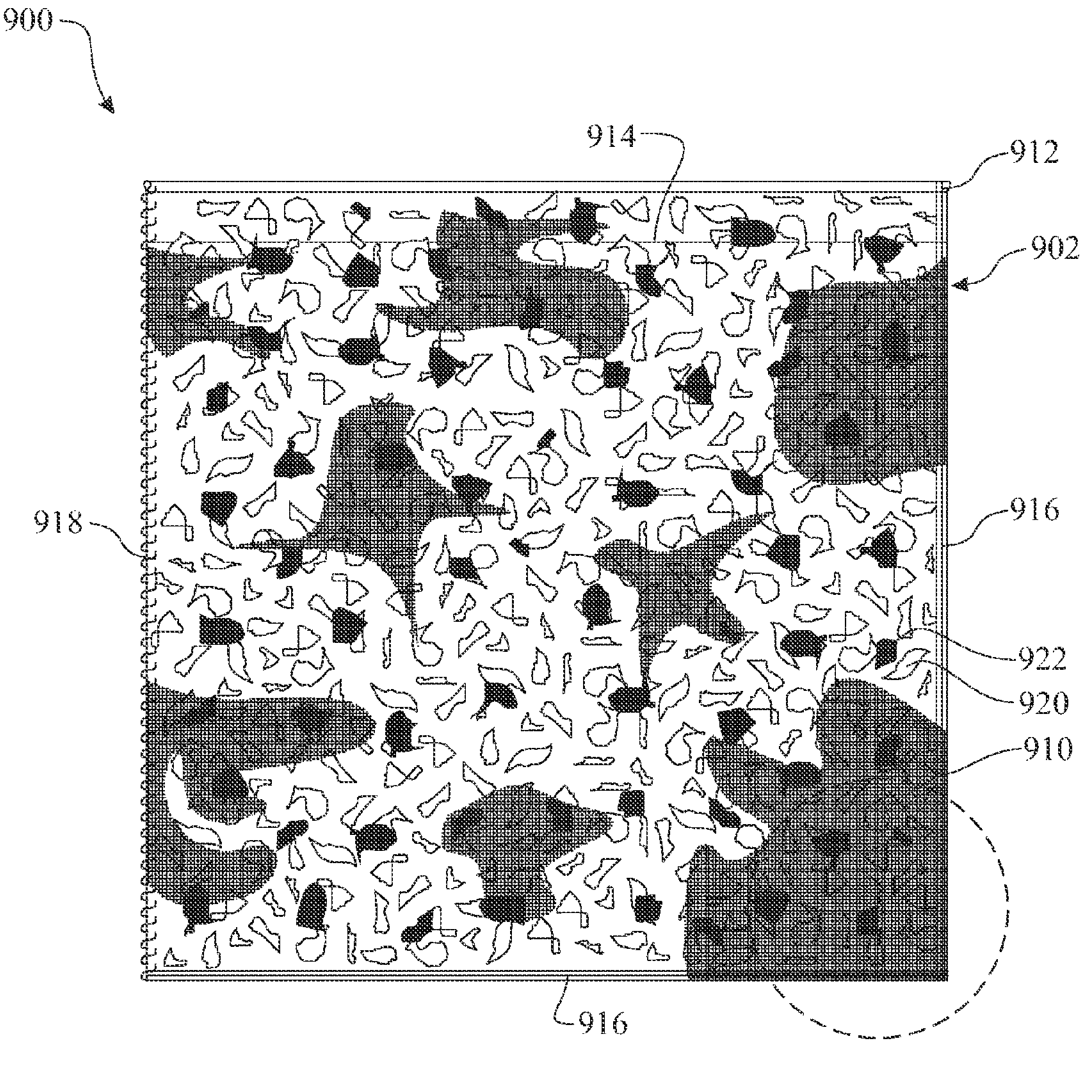
FIG. 13 presents a side elevation view of another exemplary bath water treatment dispensing packet.
Figure 14:
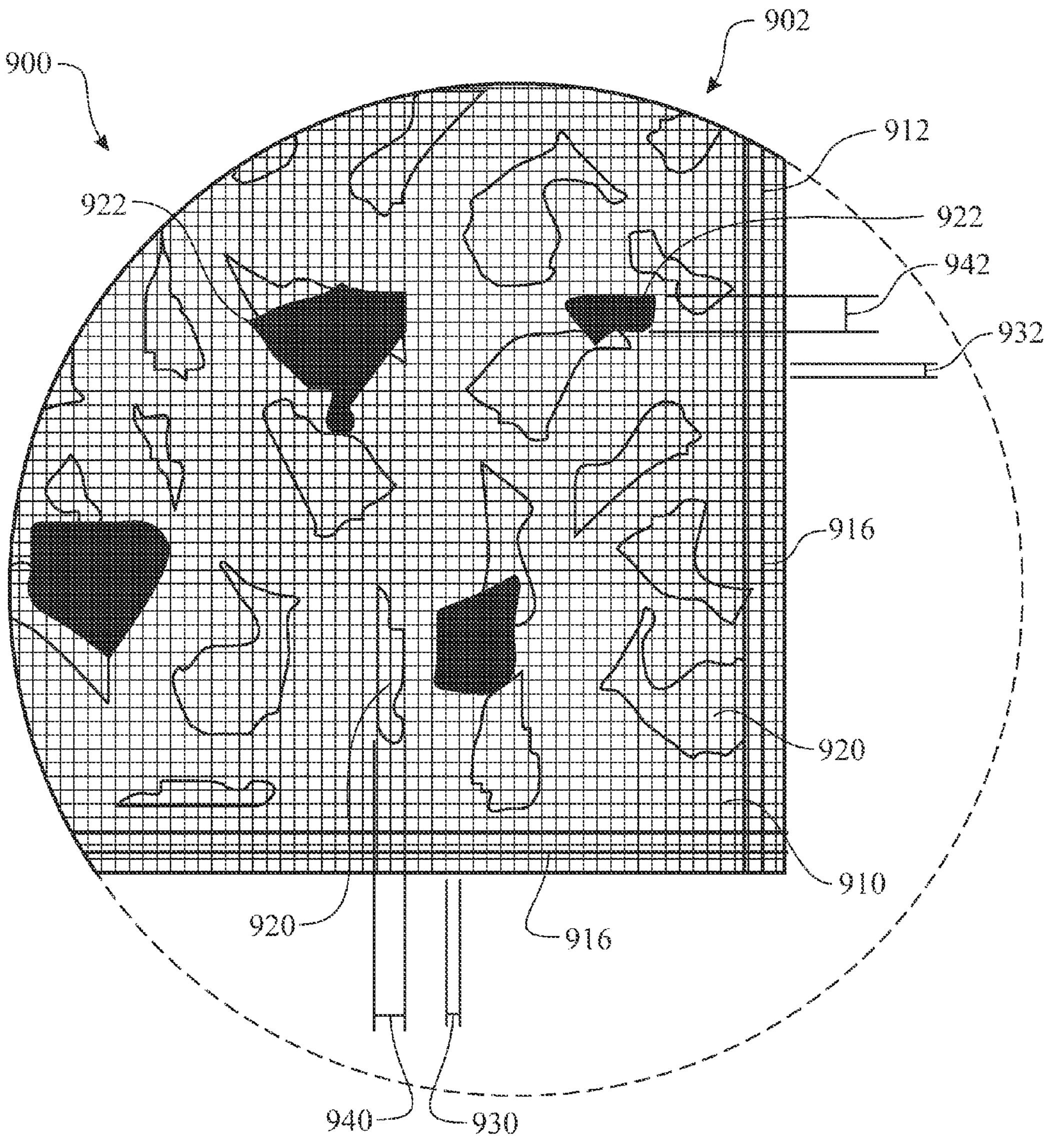
FIG. 14 presents an enlarged section of the side elevation view of the exemplary bath water treatment dispensing packet introduced in FIG. 13.

Another exemplary bath water treatment dispensing packet is referred to as a bath water treatment dispensing packet 900, as illustrated in FIGS. 13 and 14. The bath water treatment dispensing packet 900 further refines the materials of the bath water treatment dispensing packet 100. Like features of the bath water treatment dispensing packet 900 and the bath water treatment dispensing packet 100 are numbered the same except preceding by the numeral "9". The bath water treatment dispensing packet 900 is designed to maintain the salt substance 920 and the herb substance 922 within an interior of a substance containing packet 902 until use. The substance containing packet 902 additionally maintains a clean bathing experience by maintaining the herb substance 922 within the substance containing packet 902. The salt substance 920 utilizes a combination of baking soda and salts to retain the oils for aromatheraphy during packaging, sales, and storage until use. The salt substance 920 dissolves during use, releasing the oils as well as minerals and other nutrients provided by the salts and baking soda. The released oil is designed to float to the surface of the bath water, providing aromatheraphy to the bathing individual. Similarly, the herb substance 922 emits an odor into the bath water, wherein the odor provides additional contributions to the aromatheraphy. It is noted that, as the salts dissolve, the bath water treatment dispensing packet 900 transforms from being submerged to a floating object, thus exposing the quantity of herb substance 922 retained within the substance containing packet 902 at the surface of the bath water.

Details of dimensions are presented in FIG. 14. The salt substance 920 comprises a volume of individual granules of salt. Similarly, the herb substance 922 comprises a volume of flakes or pieces of flowers, herbs, or other similar compositions. Each granule 920 or flake 922 can be sized by a respective smallest dimension. The ingredients of the compositions of the salt substance 920 and the herb substance 922 are selected to have a size where the smallest dimension of each granule 920 or flake 922 (of at least a majority thereof) would be greater than a size of the apertures of the materials selected for fabricating the substance containing packet 902. In the exemplary embodiment, the substance containing packet 902 is fabricated of a first and second sheet of material or a single, folded sheet of material. The material used can be selected from any porous material. The exemplary material is a woven, porous material having a fabric mesh lateral pitch 930 and a fabric mesh longitudinal pitch 932. It is understood that this arrangement and these dimensions are only exemplary to demonstrate the size of the apertures of the material respective to the dimensions of the granules of the salt substance 920 or of the flakes of the herb substance 922. The nominal dimension of the salt substance 920 is referred to and identified as a salt minor dimension 940. The nominal dimension of the herb substance 922 is referred to and identified as a herb minor dimension 942. The salt minor dimension 940 and herb minor dimension 942 are larger than the fabric mesh lateral pitch 930 and fabric mesh longitudinal pitch 932, thus retaining the salt substance 920 and the herb substance 922 within the substance containing packet 902 until use.

Figure 15:
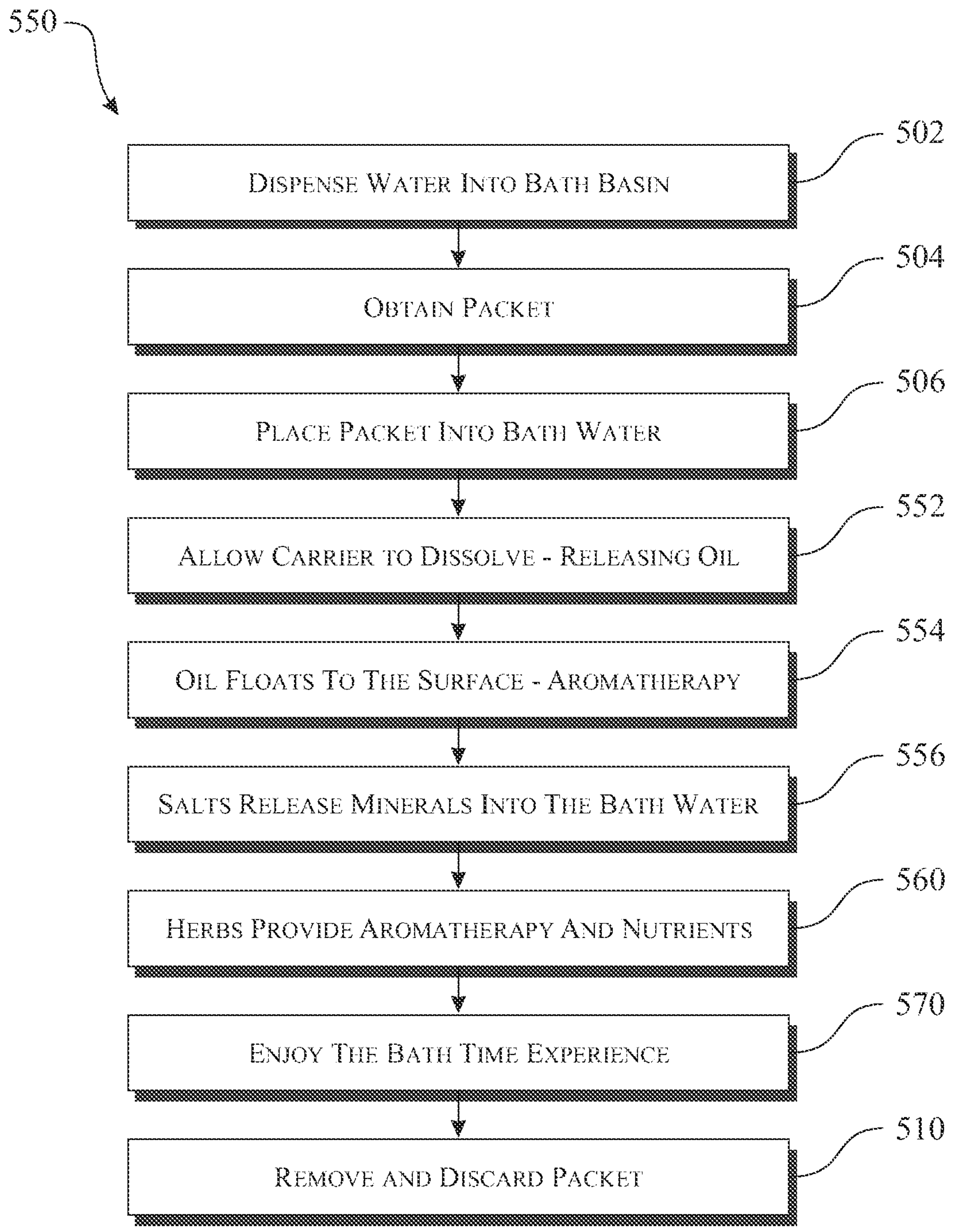
FIG. 15 presents an exemplary flow diagram of another method of use of the bath water treatment dispensing packet.

The utilization of the bath water treatment dispensing packet 900 is described in the bath additive method of use flow diagram 550 presented in FIG. 15. The bath additive method of use flow diagram 550 is similar to the bath additive method of use flow diagram 500, with common steps being described and numbered the same. The bath additive method of use flow diagram 550 initiates with a dispensing water into a bath basin step 502. The bather would determine the desired bath temperature and set the faucets/valves providing the source water accordingly. The bather would continue with a step of obtaining a bath water treatment dispensing packet 504. The bather then places the bath water treatment dispensing packet into the body of bath water 506. Upon placement of the bath water treatment dispensing packet 900 into the bath water, the oil carrier (salt substance 922 and baking soda) dissolves, releasing the oils into the bath water 552. The oil composition floats to the surface of the bath water 554. Once the oils are floating upon the surface, the oils provide aromatherapy to the bather. The dissolution of the salt composition 920 also releases minerals into the bath water. As the herb substance 922 is exposed to the water, the water draws out scents from the herb substance 922. The scents float to the water surface providing additional aromatherapy to the bather 960. It is noted that the flakes of the herb substance 922 remain within the substance containing packet 902 during the entire bathing experience, providing a clean bathing experience for the bather. The bather places themselves into the body of bath water and enjoys the experience 570 either during or subsequent to the dissolution of the salt substance 920. The bather can optionally remove and discard the packet 510 at any point during the bathing experience after dissolution of the salt substance 920.

The preferred embodiment of the bath water treatment dispensing packet 100, 200, 300, 700 utilizes all natural and biodegradable materials. The bath water treatment dispensing packet 100, 200, 300, 700, 900 can be included within a bath treatment kit including matching scented candles, matching or complimentary tea bags, organic soap, a complimentary shower gel, a travel pouch, and the like.

Although the disclosed embodiments utilize the salt substance 120 and the herb substance, the bath water treatment dispensing packet 100, 200, 300, 700, 900 can be further enhanced with the inclusion of softeners and/or other additives such as power clay, mustard, rice flour, and the like.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

REFERENCE ELEMENT DESCRIPTIONS

Ref. No. Description
100 bath water treatment dispensing packet
102 substance containing packet
110 dispensing packet material
112 material fold section
114 fold seal
116 ultrasonic seal
118 stitched seal
120 salt substance
122 herb substance
200 bath water treatment dispensing packet strip
202 dispensing packet material
210 herb compartment
212 herb substance
214 section seal
216 compartment perforation
218 stitched seal
220 salt compartment
222 salt substance
300 bath water treatment dispensing packet
302 dispensing packet material
310 herb compartment
312 herb substance
320 salt compartment
322 salt substance
330 compartment separation
332 packet shaping adhesion
400 floating packet dispenser
402 porous packet enclosure
404 floatation ring
406 packet receiving compartment
408 float base member
500 bath additive method of use flow diagram
502 dispense water into bath basin step
504 obtain packet step
506 place packet into bath water step
508 composition dissolution step
510 remove and discard packet step
512 enjoy the bath experience step
550 bath additive method of use flow diagram
552 allow oil carrier to dissolve and release oils for aromatic therapy step
554 oil floats the water surface providing aromatic therapy step
556 salts release minerals into the bath water for absorption through skin step
560 herbs provide aromatherapy and nutrients step
570 enjoy aromatic and herbal bath experience step
600 bath additive method of use flow diagram
604 obtain floating dispenser step
606 insert packet into dispenser step
608 place dispenser into bath water step
610 remove and discard dispenser and packet step
700 bath water treatment dispensing packet
710 dispensing packet material
712 packet material fold
724 oil-salt-herb composition
734 first packet side
736 second packet side
740 first packet seam edge
742 packet fill opening
750 second packet seam edge
760 third packet seam edge
770 first packet stitch
771 first stitch tail
772 second packet stitch
773 second stitch tail
774 third packet stitch
775 third stitch tail
780 tag
782 first tag side
784 second tag side
786 adhesive
788 indicia
790 sealant
800 packet fabrication flow diagram
810 composition blending process
812 blend essential oils step
814 introduce baking soda to form powder step
816 add salts to powder composition step
818 add flower and herb blend to composition step
820 packet preparation process
822 size packet material step
824 fold packet material step
826 partially enclose packet material by stitching step
830 "fill partially enclosed packet with oil, salt, scent composition"
832 seal packet closure using stitching step
834 preserve stitching by applying sealant step
836 add tag to distal end of stitching step
840 insert packet into distribution packaging step
842 bulk pack and distribute for use step
900 bath water treatment dispensing packet
902 substance containing packet

910 dispensing packet material
912 material fold section
914 fold seal
916 ultrasonic seal
918 stitched seal
920 salt substance
922 herb substance
930 fabric mesh lateral pitch
932 fabric mesh longitudinal pitch
940 salt minor dimension
942 herb minor dimension

What is claimed is:

1. A method of packaging an additive for a body of bath water, the method comprising the steps of:

forming a porous bath water treatment dispensing packet comprising a first side and a second side, having joined edges forming an interior compartment and an access opening providing access to the interior compartment;

selecting at least one aromatherapy oil from a group of aromatherapy oils consisting of: peppermint oil, lavendin oil, eucalyptus oil, geranium oil, lavender oil, chamomile oil, rosewood oil, sweet orange oil, petitgrain oil, bergamot oil, palmarosa oil, citrus petitgrain oil, and blood orange oil, wherein the selection is based upon a desired treatment;

blending a quantity of the at least one selected aromatherapy oil with a quantity of a carrier which absorbs the at least one aromatherapy oil, wherein the carrier is a solid which dissolves when immersed in the body of bath water dispersing the at least one aromatherapy oil into the body of bath water;

combining a quantity of at least one salt composition and the oil impregnated carrier to form an aromatherapy oil and salt blended composition;

combining a quantity of at least one herb composition into the aromatherapy oil and salt blended composition; and dispensing a volume of the aromatherapy oil, salt, and at least one herb blended composition into the interior compartment of the porous bath water treatment dispensing packet, wherein at least one of the first side and a second side are fabricated of a porous material enabling the solid carrier and the quantity of at least one salt composition to dissolve into the body of bath water when immersed in the body of bath water dispersing the at least one aromatherapy oil and the aromatherapy oil floats to the surface providing aromatherapy to a bather.

2. A method of packaging an additive for a body of bath water as recited in claim 1, the method further comprising a step of blending a plurality of salts, including a quantity of Epsom salt.

3. A method of packaging an additive for a body of bath water as recited in claim 1, wherein the quantity of at least one aromatherapy oil comprises up to 10 percent of the total volume of the aromatherapy oil and salt blended composition and the carrier comprises up to 8 percent of the total volume of the aromatherapy oil and salt blended composition.

4. A method of packaging an additive for a body of bath water as recited in claim 1, wherein the group of aromatherapy oils is refined into a mint based aromatherapy oil group consisting of: peppermint oil, lavendin oil, eucalyptus oil, geranium oil, and cedarwood oil;

wherein the step of selecting at least aromatherapy oil is accomplished by selected at least one aromatherapy oil from the mint based aromatherapy oil group.

5. A method of packaging an additive for a body of bath water as recited in claim 1, wherein the group of aromatherapy oils is refined into a lavender based oil group consisting of: lavender oil, chamomile oil, rosewood oil, sweet orange oil, petitgrain oil, bergamot oil, and palmarosa oil;

wherein the step of selecting at least aromatherapy oil is accomplished by selected at least one aromatherapy oil from the lavender based oil group.

6. A method of packaging an additive for a body of bath water as recited in claim 1, wherein the group of aromatherapy oils is refined into a citrus based oil group consisting of: sweet orange oil, lavender oil, citrus petitgrain oil, and blood orange oil;

wherein the step of selecting at least aromatherapy oil is accomplished by selected at least one aromatherapy oil from the citrus based oil group.

7. A method of packaging an additive for a body of bath water as recited in claim 1, wherein the aromatherapy oil carrier is baking soda.

8. A method of packaging an additive for a body of bath water as recited in claim 1, wherein the aromatherapy oil carrier is baking soda and the quantity of baking soda is between 2.0 and 8.0 percent of the total composition and the total quantity of selected aromatherapy oil or aromatherapy oils is between 0.5 and 10.0 percent of the total composition.

9. A method of packaging an additive for a body of bath water as recited in claim 1, wherein the aromatherapy oil carrier is baking soda and the quantity of baking soda is between 3.0 and 5.0 percent of the total composition and the total quantity of selected aromatherapy oil or aromatherapy oils is between 0.5 and 6.0 percent of the total composition.

10. A method of packaging an additive for a body of bath water as recited in claim 1, wherein the aromatherapy oil carrier is baking soda and the quantity of baking soda is between 3.3 and 4.5 percent of the total composition and the total quantity of selected aromatherapy oil or aromatherapy oils is between 0.5 and 3.0 percent of the total composition.

11. A method of packaging an additive for a body of bath water as recited in claim 1, wherein the aromatherapy oil carrier is baking soda and the quantity of baking soda is between 2.0 and 8.0 percent of the total composition; the total quantity of selected aromatherapy oil or aromatherapy oils is between 0.5 and 10.0 percent of the total composition; and the total quantity of salt is between 50 and 96 percent of the total composition.

12. A method of packaging an additive for a body of bath water, the method comprising the steps of:

forming a porous bath water treatment dispensing packet comprising a first side and a second side, having joined edges forming an interior compartment and an access opening providing access to the interior compartment;

selecting at least aromatherapy oil from a group of aromatherapy oils consisting of: peppermint oil, lavendin oil, eucalyptus oil, geranium oil, lavender oil, chamomile oil, rosewood oil, sweet orange oil, petitgrain oil, bergamot oil, palmarosa oil, citrus petitgrain oil, and blood orange oil, wherein the selection is based upon a desired treatment;

blending a quantity of the at least one selected aromatherapy oil with a quantity of baking soda which absorbs the at least one aromatherapy oil, wherein the baking soda dissolves when immersed in a liquid dispersing the at least one aromatherapy oil into the body of bath water;

combining a quantity of at least one salt composition and the aromatherapy oil impregnated baking soda to form an aromatherapy oil and salt blended composition;

combining a quantity of at least one herb composition into the aromatherapy oil and salt blended composition; and dispensing a volume of the aromatherapy oil, salt, and at least one herb blended composition into the interior compartment of the porous bath water treatment dispensing packet, wherein at least one of the first side and a second side are fabricated of a porous material enabling the solid carrier and the quantity of at least one salt composition to dissolve into the body of bath water when immersed in the body of bath water dispersing the at least one aromatherapy oil and the aromatherapy oil floats to the surface providing aromatherapy to a bather.

13. A method of packaging an additive for a body of bath water as recited in claim 12, the method further comprising a step of blending a plurality of salts, including a quantity of Epsom salt.

14. A method of packaging an additive for a body of bath water as recited in claim 12, wherein the quantity of at least one aromatherapy oil comprises up to 10 percent of the total volume of the aromatherapy oil and salt blended composition and the baking soda comprises up to 8 percent of the total volume of the aromatherapy oil and salt blended composition.

15. A method of packaging an additive for a body of bath water as recited in claim 12, wherein the group of aromatherapy oils is refined into a mint based aromatherapy oil group consisting of: peppermint oil, lavendin oil, eucalyptus oil, geranium oil, and cedarwood oil;

wherein the step of selecting at least aromatherapy oil is accomplished by selected at least one aromatherapy oil from the mint based aromatherapy oil group.

16. A method of packaging an additive for a body of bath water as recited in claim 12, wherein the group of aromatherapy oils is refined into a lavender based oil group consisting of: lavender oil, chamomile oil, rosewood oil, sweet orange oil, petitgrain oil, bergamot oil, and palmarosa oil;

wherein the step of selecting at least aromatherapy oil is accomplished by selected at least one aromatherapy oil from the lavender based oil group.

17. A method of packaging an additive for a body of bath water as recited in claim 12, wherein the group of aromatherapy oils is refined into a citrus based oil group consisting of: sweet orange oil, lavender oil, citrus petitgrain oil, and blood orange oil;

wherein the step of selecting at least aromatherapy oil is accomplished by selected at least one aromatherapy oil from the citrus based oil group.

18. A method of packaging an additive for a body of bath water as recited in claim 12, wherein the aromatherapy oil carrier is baking soda.

19. A method of packaging an additive for a body of bath water as recited in claim 12, wherein the aromatherapy oil carrier is baking soda and the quantity of baking soda is between 2.0 and 8.0 percent of the total composition and the total quantity of selected aromatherapy oil or aromatherapy oils is between 0.5 and 10.0 percent of the total composition.

20. A method of packaging an additive for a body of bath water as recited in claim 12, wherein the aromatherapy oil carrier is baking soda and the quantity of baking soda is between 3.0 and 5.0 percent of the total composition and the total quantity of selected aromatherapy oil or aromatherapy oils is between 0.5 and 6.0 percent of the total composition.

21. A method of packaging an additive for a body of bath water as recited in claim 12, wherein the aromatherapy oil carrier is baking soda and the quantity of baking soda is between 3.3 and 4.5 percent of the total composition and the total quantity of selected aromatherapy oil or aromatherapy oils is between 0.5 and 3.0 percent of the total composition.

22. A method of packaging an additive for a body of bath water as recited in claim 12, wherein the aromatherapy oil carrier is baking soda and the quantity of baking soda is between 2.0 and 8.0 percent of the total composition; the total quantity of selected aromatherapy oil or aromatherapy oils is between 0.5 and 10.0 percent of the total composition; and the total quantity of salt is between 50 and 96 percent of the total composition.

* * * * *